United States Patent [19]

Kulvi

[11] 4,084,589
[45] Apr. 18, 1978

[54] URINE COLLECTION APPARATUS

[76] Inventor: Ruth L. Kulvi, 3337 Cockator Rd., Augusta, Ga. 30907

[21] Appl. No.: 693,648

[22] Filed: Jun. 7, 1976

[51] Int. Cl.² .......................... A61F 5/44; A61M 1/00
[52] U.S. Cl. ..................................... 128/278; 128/295
[58] Field of Search .............. 128/295, 297, 277, 278, 128/281, 294, 299, 276, 2 F, 2 G, DIG. 5, 283, 272, 275, 275.1, DIG. 27, DIG. 24; 4/99, 10, 110, 112; 220/13; 62/457, 261

[56] References Cited

U.S. PATENT DOCUMENTS

| | | | |
|---|---|---|---|
| 2,548,149 | 4/1951 | Fowler | 128/295 |
| 2,944,551 | 7/1960 | Breer | 128/295 |
| 3,066,672 | 12/1962 | Crosby et al. | 128/276 |
| 3,077,883 | 2/1963 | Hill | 128/295 |
| 3,112,061 | 11/1963 | Breer | 128/278 X |
| 3,401,697 | 9/1968 | Lefley et al. | 128/295 |
| 3,405,714 | 10/1968 | Moss | 128/295 |
| 3,480,015 | 11/1969 | Gonzalez | 128/276 |
| 3,626,941 | 12/1971 | Webb | 128/283 |
| 3,743,130 | 7/1973 | Jorgensen | 220/13 X |
| 3,832,862 | 9/1974 | Ingels | 62/261 X |

OTHER PUBLICATIONS

"Surgical Equipment and Supplies" Apr.–May 1971, p. 15, Uri-Meter.

Primary Examiner—Robert W. Michell
Assistant Examiner—Michael H. Thaler
Attorney, Agent, or Firm—Browdy and Neimark

[57] ABSTRACT

An apparatus for taking a twenty-four hour urine collection, particularly for infants or very young children. A urine collection bag is air-tightly adhesively attached to the patient over the urinary area in a position to receive the urine. A pair of tubes are attached to the bag, one of which is an air supply tube and is connected between the upper end of the bag and the outlet of an air pump. The other tube is a drainage tube and is connected between the bottom of the bag and the top of a graduated cylindrical container supported over an ice bucket. Another tube connects the top end of the container to the inlet of the air pump, thus providing air flow through the bag which induces suction and aspirates the urine entering the bag into the drainage tube and thence to the cylindrical container, and keeps the interior of the bag substantially dry.

10 Claims, 4 Drawing Figures

U.S. Patent
April 18, 1978
4,084,589
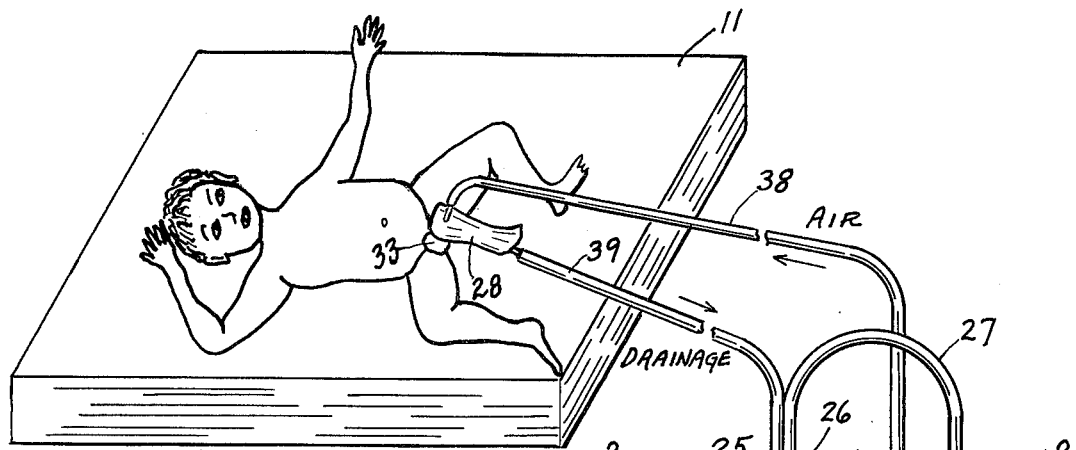
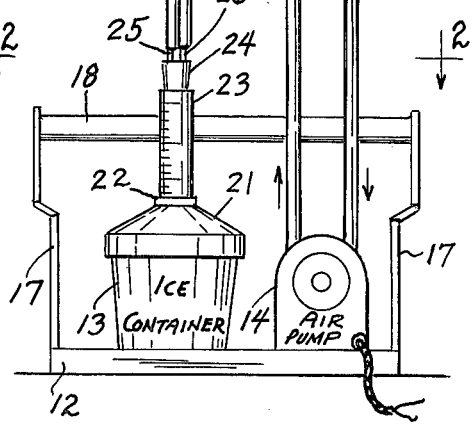
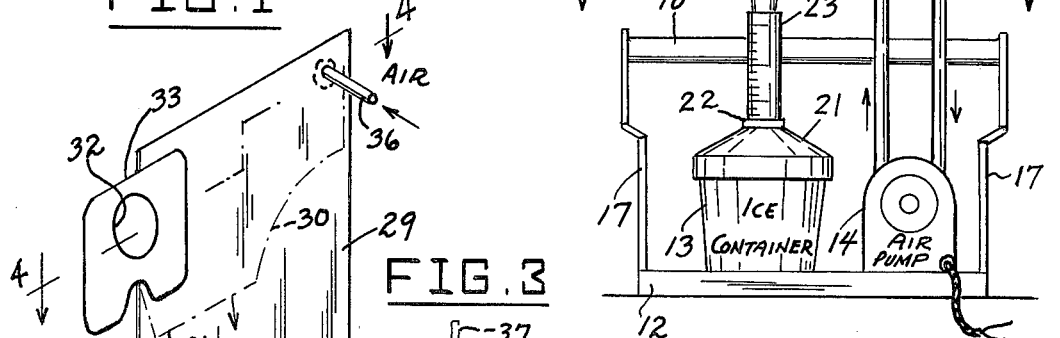
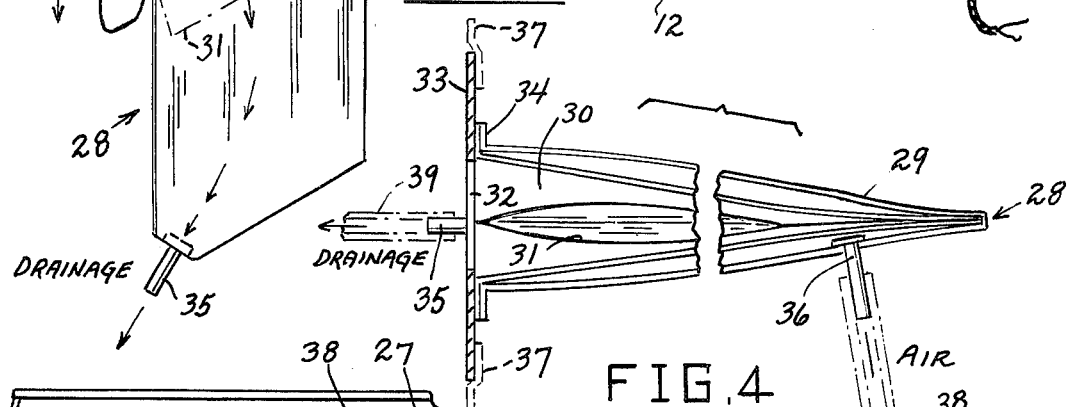
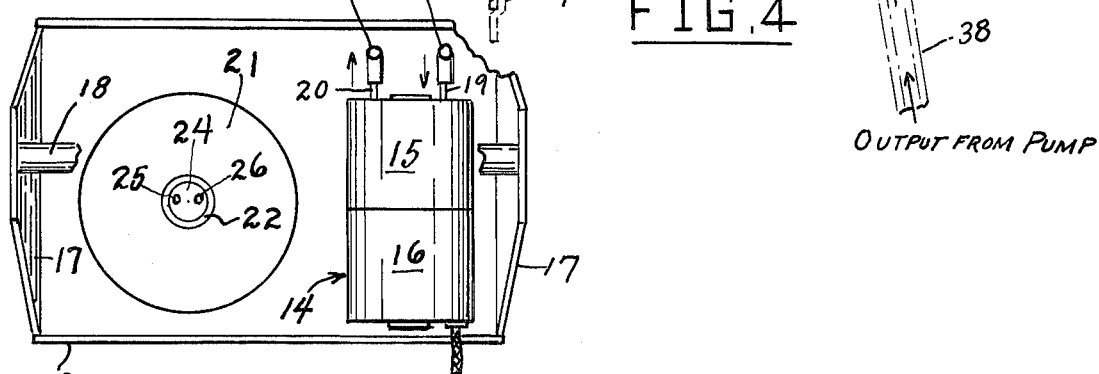

URINE COLLECTION APPARATUS

FIELD OF THE INVENTION

This invention relates to devices for collecting urine for medical purposes, and more particularly to a urine collection apparatus especially adapted for infants, very young children, or aged or handicapped patients.

BACKGROUND OF THE INVENTION

Quantitative urine collections are requested frequently for infants or very young children, or for other types of patients, such as aged or handicapped persons. For example, for infants, it may be required to collect urine specimens for several twenty-four hour periods for use in diagnosing and evaluating various conditions, such as: failure to thrive, adreno-genito syndrome, neuroblastoma, diabetes, cardiac conditions, renal disease, and metabolic and endocrine disorders. Therefore, it is imperative that accurate quantitative urine samples be collected for a twenty-four hour period. Since infants or very young children are too young to cooperate, it is necessary to employ a mechanical method and means to collect the necessary urine specimens, with due regard for the safety and comfort of the patients.

In the prior art, several different methods of collecting quantitative urine specimens have been and are presently employed. One method of collecting urine from an infant or very young child is by applying a plastic urine-collecting bag to the child. The plastic bag may have a catheter inserted into it which is used to empty the contents after the child has voided. A second method is to employ a twenty-four hour plastic urine-collecting bag which has a drain tube leading to a receptacle (as manufactured by Hollister, Inc., Chicago, Illinois). The main problem with these methods is loss of urine, necessitating the restarting of the quantitative urine collection procedure sometimes as much as two or three times, and frequently more, thereby keeping the child in the hospital for a long period of time and thereby delaying an accurate diagnosis. Other problems include disturbance of the patient by reapplication of the urine bags, excoriation of the skin due to moisture, and the need for constant restraint of all four extremities.

A third method involves the use of a modified isolette and/or crib, and is currently being used at the National Institute of Health. A fourth method, frequently used to collect urine, involves a "metabolic mattress" (with one or two holes in the mattress). The mattress is difficult to keep clean, and both of these methods are quite expensive.

Pump-operated urine collectors have been also proposed and have been experimentally successful in some cases, but in all cases have been excessively cumbersome and awkward.

SUMMARY OF THE INVENTION

Accordingly, a main object of the invention is to provide a novel and improved apparatus of the type employing a plastic urine-collecting bag for collecting twenty-four hour samples of urine from infants, very young children, or handicapped patients, utilizing pump operation, and being relatively compact in size, being easy to install, requiring minimal restraint of the patient, involving little chance of contamination, producing minimum loss of sample, providing quantitatively accurate collection of urine, and enabling parents or others to hold a child for feeding or other activities while the apparatus is in operation.

A further object of the invention is to provide an improved apparatus for obtaining quantitatively accurate urine samples from infants, young children, or relatively incapacitated patients, the apparatus employing simple and easily obtainable components, requiring no special mattresses or other furniture, requiring no restraints of the patient's extremities, causing minimal excoriation of the patient's skin due to moisture, and employing a plastic collection bag which is under continuous suction, thus keeping the bag empty of urine, keeping the patient's skin area exposed to the bag dry, and minimizing loss of sample, thereby insuring accurate collection of the urine.

BRIEF DESCRIPTION OF THE DRAWINGS

Further objects and advantages of the invention will become apparent from the following description and claims, and from the accompanying drawings, wherein:

FIG. 1 is a perspective view of an infant with a urine-collecting apparatus according to the present invention connected to the infant.

FIG. 2 is a fragmentary enlarged horizontal cross-sectional view taken substantially on line 2—2 of FIG. 1.

FIG. 3 is an enlarged perspective view of a typical plastic urine-collecting bag employed with the apparatus shown in FIG. 1.

FIG. 4 is an enlarged horizontal cross-sectional view taken substantially on line 4—4 of FIG. 3.

DESCRIPTION OF A PREFERRED EMBODIMENT

Referring to the drawings, a child whose urine is to be collected is supported on a conventional mattress 11 in a crib or on a bed, or in any other suitable supporting enclosure. Adjacent to the crib or bed, for example on the floor, or on a suitable support spaced well below the level of mattress 11, is provided a tray 12 on which is supported an ice bucket 13 and an electric air pump assembly 14 comprising an air pump 15 and an electric driving motor 16 connected to the pump. Tray 12 is provided with upstanding opposite end wall members 17, 17 whose top ends are connected by a carrying bar 18. Air pump 15 has the air inlet connection conduit 19 and the air outlet connection conduit 20.

The ice bucket 13 is provided with a generally frusto-conical flanged top cover 21 having a central top opening surrounded by an annular upstanding collar 22 in which is slidably received a graduated cylindrical container 23 which is supported thereby in a vertical upstanding position with its bottom end in contact with ice in the bucket 13. A rubber cork member 24 is provided in the top end of cylindrical container 23, said cork member having a pair of vertical bores in which are sealingly engaged the respective rigid glass connection conduits 25, 26 which thus communicate with the top portion of container 23. Connection conduit 26 is connected to pump inlet conduit 19 by a flexible tube 27.

Designated generally at 28 is a flexible plastic urine collection bag which comprises a main outer flexible plastic receptacle 29 which may be of generally rectangular shape, as shown in FIG. 3, and which may comprise clear flexible plastic sheet material. The upper portion of the receptacle includes a downwardly opening guide conduit member 30 having the normally closed bottom aperture 31, said aperture 31 being shown in open flow-responsive condition in FIG. 4. The upper side portion of guide conduit member 30 communicates with and is sealed around a generally oval aperture 32 formed in an attachment card member 33, the upper adjacent side wall portions of member 29 being likewise sealingly secured circumferentially around said aperture 32, as shown at 34 in FIG. 4.

A tubular drainage conduit connector 35 is provided at the bottom of collection bag 28 and a tubular air inlet conduit connector 36 is provided at the top portion of said collection bag, as shown in FIG. 3.

The attachment card member 33 is adapted to be sealingly attached to the perineal area of the child around the penis or vagina, which is thus received in the opening 32 so as to allow urine to be voided into the guide conduit member 30 and then to flow through the yieldable bottom opening 31 into the lower portion of main receptacle 29.

In applying the collection bag 28 to the child, tincture of benzoin is first applied to the perineal area, after which the connection card member 33 is applied to the perineum with the penis or vagina received in the opening 32 and the card member 33 is then air-tightly sealed to the skin around the margins of the card member, for example, by means of masking tape, shown in dotted view at 37 in FIG. 4. It is essential that there be an air-tight connection between the periphery of the card member 33 and the skin, in order to prevent leakage.

After the collection bag 28 has thus been applied to the child, a flexible air inlet tube 38 is employed to connect the conduit member 36 to the pump outlet conduit 20, and a flexible urine drainage tube 39 is employed to connect the bag drainage conduit member 35 to the glass connection conduit 25 leading into container 23. The pump motor 16 may then be energized. The air-tightness of the bag 28 can be tested by pinching conduit 39 to close same for a few seconds, whereby the bag 28 will inflate if air-tight. This procedure also primes the bag with air.

If the bag does not inflate or is leaking air or urine, reinforcement of the seal of the periphery of card member 33 by additional masking tape may be necessary. A small cotton ball or piece of cotton can be fastened in required areas to provide the necessary pressure to hold the masking tape in place.

As above mentioned, the tray 12 must be located well below the mattress 11. The tray may be placed on the floor adjacent the crib or bed containing the child, or may be placed on a chair or small table suitably spaced from the crib or bed.

When urine is voided, it enters the member 30 and is immediately drawn downwardly through the yieldable bottom opening 31 and the lower portion of receptacle 29 into tube 39 by the suction developed in tube 39 by the air circulating as a result of the action of the pump 15. The urine is thus immediately delivered to the graduated container 23, and the urine is collected in said container 23 as long as the apparatus remains in operation. Thus, there is no loss of urine, and the interior of the receptacle 29 is maintained substantially dry, minimizing excoriation of the skin area exposed to said receptacle interior.

While a specific embodiment of an improved urine collection apparatus has been disclosed in the foregoing description, it will be understood that various modifications within the spirit of the invention may occur to those skilled in the art. Therefore it is intended that no limitations be placed on the invention except as defined by the scope of the appended claims.

What is claimed is:

1. A urine collection apparatus comprising a bag formed of thin flexible plastic material having a urine-receiving opening at its top end portion, adhesive means surrounding said urine-receiving opening to adhesively sealingly secure said bag to a patient in a position to receive urine through said opening with the bag sealed to the patient's skin around said opening, an upstanding urine-receiving precision graduated volumetric measurement container, air pump means, drainage conduit means communicatively connecting the lower end portion of the bag to the top end portion of said upstanding container, air circulation conduit means communicatively connecting the top end portion of said container to the inlet of said air pump means, air supply conduit means communicatively connecting the outlet of said air pump means to the top end portion of said bag, whereby to provide air flow downwardly through said bag to induce suction therein and to draw urine voided by the patient through said opening into said upstanding container through said drainage conduit means and to keep the interior of said bag dry, and refrigerated support means supportingly receiving said upstanding container.

2. A urine collection apparatus comprising a bag formed of thin flexible plastic material having a urine-receiving opening at its top end portion, adhesive means surrounding said urine-receiving opening to adhesively sealingly secure said bag to a patient in a position to receive urine through said opening with the bag sealed to the patient's skin around said opening, an upstanding urine-receiving graduated volumetric measurement container, air pump means, drainage conduit means communicatively connecting the lower end portion of the bag to the top end portion of said upstanding container, air circulation means communicatively connecting the top end portion of said container to the inlet of said air pump means, air supply conduit means communicatively connecting the outlet of said air pump means to the top end portion of said bag, whereby to provide air flow downwardly through said bag to induce suction therein and to draw urine voided by the patient through said opening into said upstanding container through said drainage conduit means and to keep the interior of said bag dry, and a vessel containing refrigerating material supportingly receiving said graduated receptacle.

3. The urine collection apparatus of claim 2, and wherein said upstanding container comprises a substantially vertical graduated cylindrical receptacle.

4. The urine collection apparatus of claim 3, and wherein said bag is provided in its upper portion with a flexible downwardly-opening internal guide conduit leading from said urine-receiving opening to the lower portion of the bag.

5. The urine collection apparatus of claim 4, and wherein said means to secure said bag to a patient includes a card-like member secured to the bag and surrounding said urine-receiving opening and being adapted to be sealingly secured to the patient's skin around the periphery of said card-like member.

6. A urine collection apparatus, comprising a bag formed of thin flexible plastic material having a urine-receiving opening at its top end portion, means to adhesively sealingly secure said bag to a patient in a position to receive uring through said opening with the bag sealed to the patient's skin around said opening, an upstanding urine-receiving precision volumetric measurement container, air pump means, drainage conduit means communicatively connecting the lower end portion of the bag to the top end portion of said upstanding container, air circulation means communicatively connecting the top end portion of said container to the inlet of said air pump means, air supply conduit means communicatively connecting the outlet of said air pump means to the top end portion of said bag, whereby to provide air flow downwardly through said bag to induce suction therein and to draw urine voided by the patient through said opening into said upstanding container through said drainage conduit means and to keep the interior of said bag dry, and an ice bucket provided with a top cover having a central aperture, said upstanding container being supportingly received in said central aperture.

7. The urine collection apparatus of claim 6, and wherein said apparatus includes a portable tray member, and wherein said air pump means and said upstanding urine-receiving container are supported on said portable tray member.

8. The urine collection apparatus of claim 6, and wherein said upstanding container comprises a graduated substantially vertical cylindrical receptacle.

9. The urine collection apparatus of claim 8, and wherein said upstanding container is provided with a cork member in its top end, said cork member having a pair of rigid conduits engaged vertically therethrough, said drain conduit means and air circulation means being respectively connected to said rigid conduits.

10. A urine collection device particularly adapted for use with children, and for collecting precise quantities of uncontaminated urine, comprising a bag formed of thin flexible plastic material having a urine-receiving opening at its top end portion, means to adhesively sealingly secure said bag to a patient in a position to receive urine through said opening with the bag sealed to the patient's skin around said opening, said bag having a urine outlet at its lower end and an air inlet opening at its top portion;

urine receiving and measuring means to receive and precisely measure the amount of urine passing into said bag;

drainage conduit means to pass the urine from the urine outlet of said bag to said urine receiving and measuring means;

means to provide air flow to said bag through said air inlet opening to induce flow of urine out of said bag and through said drainage conduit and to keep the interior of said bag dry, said means comprising an air pump and an air conduit passing from said air pump to the air inlet opening at the top end portion of said bag; and means to cool said urine receiving and measuring means.

* * * * *